United States Patent [19]

Grisar et al.

[11] 4,099,873

[45] Jul. 11, 1978

[54] ARRANGEMENT FOR THE SPECTRAL ANALYSIS OF SUBSTANCES

[75] Inventors: Ulrich Grisar; Wilhelm Berstermann, both of Georgsmarienhütte, Fed. Rep. of Germany

[73] Assignee: Klockner-Werke AG, Fed. Rep. of Germany

[21] Appl. No.: 665,770

[22] Filed: Mar. 10, 1976

[30] Foreign Application Priority Data

Mar. 26, 1975 [DE] Fed. Rep. of Germany ....... 2513358

[51] Int. Cl.² ........................... G01J 3/30; G01J 3/12
[52] U.S. Cl. ........................................ 356/86; 356/79; 356/99
[58] Field of Search ...................... 356/74, 76, 79, 80, 356/86, 99, 100, 101

[56] References Cited

U.S. PATENT DOCUMENTS

| 2,279,646 | 4/1942 | Smith | 356/79 |
|---|---|---|---|
| 2,837,959 | 6/1958 | Saunderson et al. | 356/80 |
| 3,277,774 | 10/1966 | Landon et al. | 356/74 |

FOREIGN PATENT DOCUMENTS

| 1,050,528 | 12/1966 | United Kingdom | 356/74 |

*Primary Examiner*—Vincent P. McGraw

*Attorney, Agent, or Firm*—Michael J. Striker

[57] ABSTRACT

An arrangement of the Rowland character includes a support and a concave grating on the support for producing the spectrum characteristic of a sample being investigated. The support has a series of slits thereon which are positioned on the Rowland circle and are adjusted to the spectral lines of samples to be investigated. An element on the support is provided with a primary slit for directing the radiation derived from a sample being investigated onto the concave grating. The primary slit is positioned on the Rowland circle and the element provided with the primary slit is mounted on the support for movement along the arc of the Rowland circle. The element is mounted in such a manner as to be arrestable in a plurality of positions. The element is favorably in the form of a plate. A preferred embodiment contemplates the provision of a pair of grooves in the support, which latter may be in the form of a housing, with the grooves following the curvature of the Rowland circle and the element being guided in the grooves. The edges of the element located in the grooves may be provided with openings in which there are accommodated spherical members as well as biasing elements for urging the spherical members into contact with the grooves.

7 Claims, 6 Drawing Figures

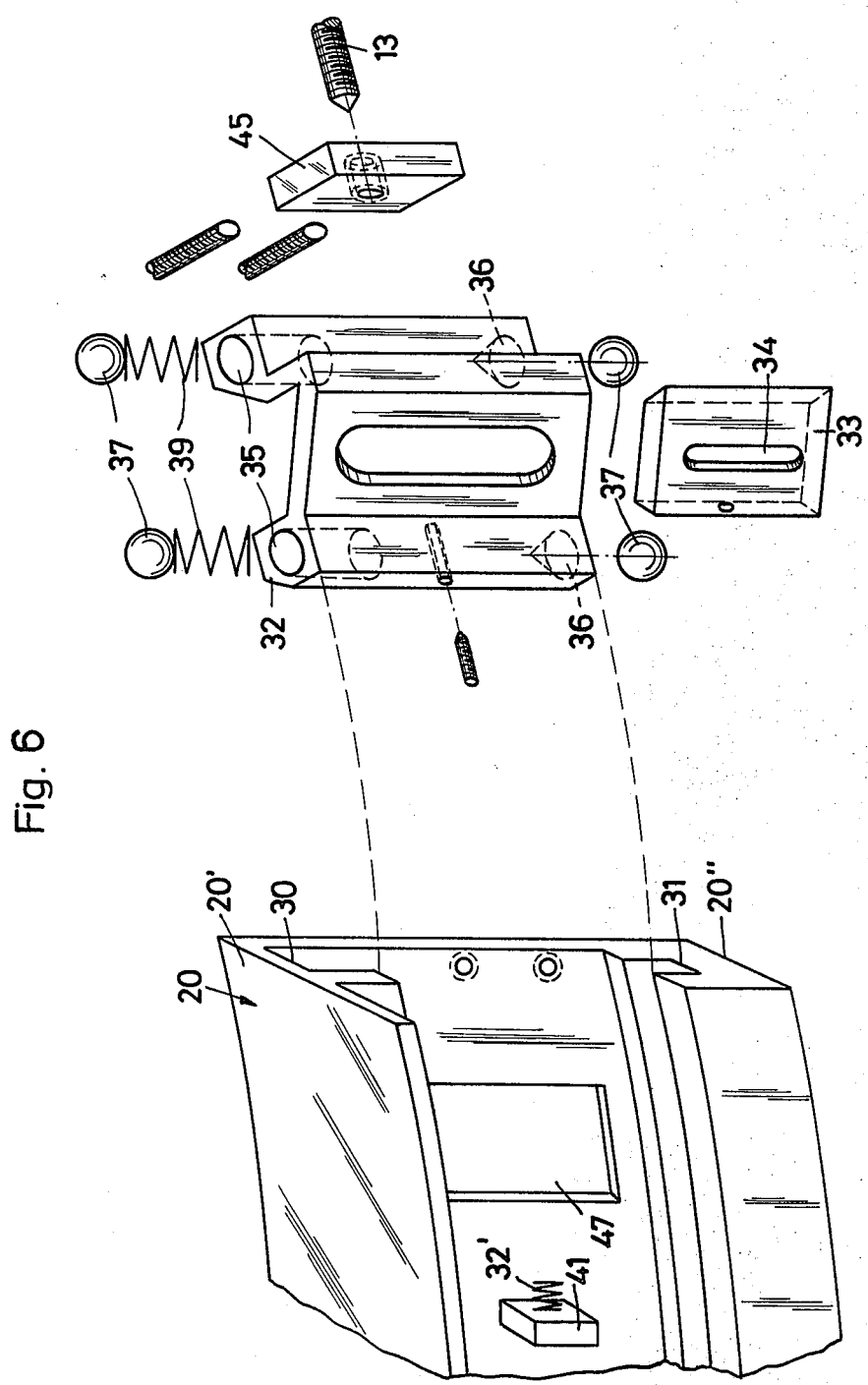

Fig. 4
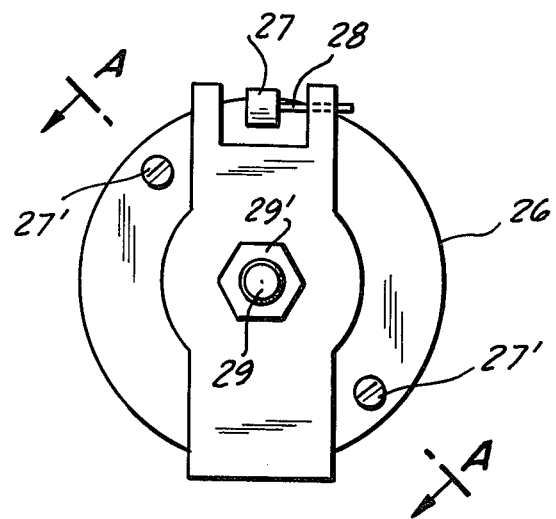
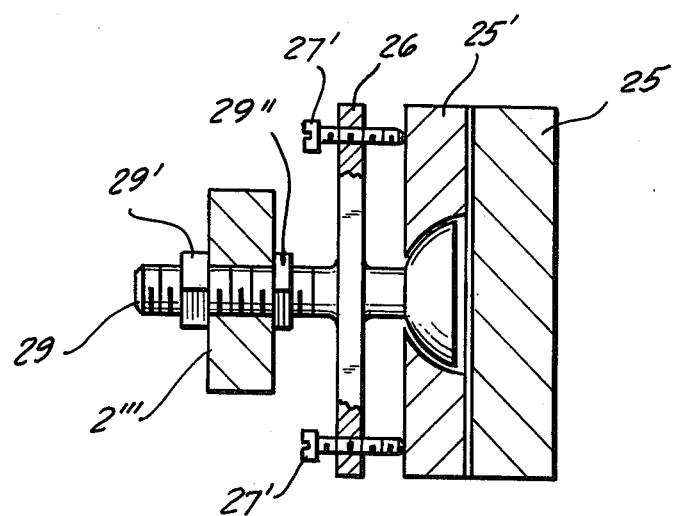
Fig. 5

ARRANGEMENT FOR THE SPECTRAL ANALYSIS OF SUBSTANCES

CROSS-REFERENCE TO RELATED APPLICATIONS

This application is related to the copending applications Ser. Nos. 665,771-665,774 filed Mar. 10, 1976.

BACKGROUND OF THE INVENTION

The invention relates generally to an arrangement for the spectral analysis of substances. Of particular interest to the invention is an arrangement for use in the determination of the alloying components of metals by spectral analysis.

A known arrangement of this type includes a primary slit and a concave diffraction grating as well as a series of secondary slits which are arranged on a circle. The positions of the secondary slits correspond to the spectral lines which are to be investigated. In operation, a spark discharge is generated between a suitable electrode and a metallic sample to be investigated. The radiation thus produced is directed onto the diffraction grating via the primary slit and the diffraction grating then produces a spectrum or series of spectral lines which are characteristic of the sample being investigated. The intensity of the lines is measured with photographic detectors. The latter generate signals which provide a measure of the proportions of the different elements in the sample.

The spectrum-forming properties of concave gratings are defined by their astigmatism.

In a plane transverse to the lines or rulings of a grating, the image locations lie on a circle, the so-called Rowland circle, when the primary slit likewise lies on this circle. The circle is tangent to the surface of the grating at the center of the concave grating and the diameter of the circle equals the radius of curvature of the concave grating. In a plane parallel to the lines or rulings of the grating, the image points are not clearly formed on the circle and the primary slit must be adjusted so as to be precisely parallel to the lines or rulings of the grating if the resolving power of the grating is not to be reduced.

The currently known spectrometers for determining the compositions of metallic alloys and similar materials, also known as quantometers, and which operate with concave gratings have large dimensions. Accordingly, they are constructed in the form of stationary apparatus for laboratory operation. The large dimensions are, above all, a result of the fact that circle diameters of less than about 1 meter have not been used heretofore. The reason resides in the previously held conception that, if a circle diameter of less than about 1 meter were used, the adjustment of the primary slit would be either impossible or else so complicated that it would only be possible to operate in scientific institutes with suitable specialists.

The adjustment of the primary slit must be effected very carefully and with great precision. In order to accomplish this, the primary slit in the known spectrometers is positioned, for example, on a swiveling arm which is supported on a pivot in the vicinity of the entry window provided for the purpose of permitting the radiation from the spark discharge to travel to the grating for resolution into a spectrum. On the other hand, the primary slit may be mounted so as to be linearly displaceable with a spindle. For the small corrections which are necessary, the large radius of curvature of the Rowland circle makes it possible, as a first aprroximation, to consider the arc in the region of the primary slit as a linear section. The relatively simple adjustment of the slit which thus becomes possible has, however, associated with it the disadvantage of operating satisfactorily only in spectrometers having a grating of long focal length and, concomitantly, a large Rowland circle.

In addition to the considerations outlined above, a satisfactory production of the spectrum requires that the sparks always be generated at exactly the same location. According to the current state of the art, this is achieved with the so-called Petrey table which is frequently provided with a protective housing against high-voltage shocks.

The large dimensions of the known spectrometers which are mounted so as to be stationary generally do not pose a disadvantage for the spectrometers. The reason resides in that a portion of the spectral lines to be investigated lie in the short wavelength ultraviolet range of the spectrum. Since the short wavelength ultraviolet rays are absorbed by air, the spectrometer itself must be evacuated and for this purpose large auxiliary apparatus is required. Thus, the combination of the spectrometer and the auxiliary apparatus would have large dimensions even if th dimensions of the spectrometer were relatively small.

In those cases where it is intended to analyze substances in order to determine alloying components having usable spectral lines which lie in the visible or long wavelength ultraviolet regions, the auxiliary apparatus for the so-called vacuum ultraviolet are not necessary.

Such an "air device" is not as universally applicable as the "vacuum quantometer" since certain elements cannot be detected. Nevertheless, it offers great advantages in the quality control of materials, both for the producer and the user of the materials. For instance, a producer or a user may be interested in sorting out in a simple manner those bars in a bundle of bars to be delivered which have proportions of alloying components different from the required proportions. However, it is always necessary to bring the individual bars, or discs cut from these bars, to the spectrometer since, as outlined above, the known spectrometers of the type under discussion cannot be transported to the workpieces to be investigated. In particular, it is not possible, for instance, to bring such spectrometers into position above a conveyor belt containing the workpieces to be analyzed so that those workpieces having a composition different from the required or predetermined composition may be registered and sorted out.

SUMMARY OF THE INVENTION

It is an object of the invention to provide a device of the character outlined above which is of such a nature that the diameter of the Rowland circle may be chosen so as to be small and an exact adjustment of the primary slit may nevertheless be obtained.

This object, as well as others will become apparent as the description proceeds, are achieved in accordance with the invention. According to one aspect of the invention, there is provided an arrangement of the Rowland character for the spectral analysis of substances, particularly for use in the determination of the composition of metallic alloys and similar materials, which includes a support and a concave grating on the support for producing the spectrum characteristic of a sample being investigated. The support has a series of slits thereon positioned on the Rowland circle and adjusted to the spectral lines of samples to be investigated. An element or carrier is provided on the support and has a primary slit for directing the radiation derived from a sample being investigated onto the concave diffraction grating. The primary slit is positioned on the Rowland circle and the element or carrier is mounted on the support for movement along the arc of the Rowland circle. The element or carrier, which advantageously includes a member of plate-like configuration, is favorably mounted so as to be arrestable in any one of a plurality of positions.

It has already been mentioned that the invention is particularly interested in a device for the determination of the alloying components of metals by spectral analysis. As will be appreciated, the invention relates, in a preferred aspect, to a device having a primary slit, a concave diffraction grating and a series of secondary slits which are arranged on a circle and the positions of which correspond to the spectral lines to be investigated. A suitable electrode is provided and, in operation, a spark discharge is generated between the electrode and a metallic sample to be investigated. The radiation from the spark discharge is directed onto the concave grating via the primary slit and the grating then produces a spectrum or series of spectral lines characteristic of the sample being investigated. The intensity of the lines may be measured with photographic detectors, which latter may generate signals providing a measure of the proportions of the different elements in the sample.

The arrangement or device of the invention makes it possible to select the diameter of the Rowland circle so as to be small while nevertheless permitting a precise adjustment of the primary slit to be achieved. This has the result that such a spectrometer formed in accordance with the invention may be readily constructed as a transportable device when it operates only in the visible and near ultraviolet spectral regions. In particular, a spectrometer of this type may, together with the spark gap for the spark discharge, be arranged above a conveyor belt.

The support of the arrangement according to the invention may include a housing and, in accordance with a preferred embodiment of the invention, the objects of the invention are achieved in that a plate provided with the primary slit is movably arranged on the arc of the Rowland circle interiorly of the housing and is mounted so as to be capable of being arrested in any one of a plurality of positions. By virtue of this construction, there is achieved the result that an adjustment or alignment of the primary slit continuously occurs on the circle and parallel thereto. Consequently, it is no longer necessary to select the diameter of the circle to be so large that, as a first approximation, an arc segment thereof may be considered to be a linear section for the purpose of alignment of the primary slit.

In a particularly advantageous embodiment of the invention, the plate with the primary slit is guided in two grooves which follow the curvature of the Rowland circle and the plate is capable of being arrested in the grooves. By virtue of this guidance, an adjustment or alignment along the circle may be insured, on the one hand, while it becomes possible, on the other hand, to achieve a mounting of the slit which is not affected by vibrations. An alignment of the slit which is not susceptible to vibrations may, for example, be favorably achieved by the provision of spherical members in those edges of the plate or carrier therefor which are covered by the grooves. The spherical members are arranged so as to roll in the grooves upon displacement of the plate or carrier with the primary slit. One or more biasing elements are provided and the spherical members are subjected to the action of the biasing elements.

The novel features which are considered as characteristic for the invention are set forth in particular in the appended claims. The invention itself, however, both as to its construction and its method of operation, together with additional objects and advantages thereof, will be best understood from the following description of the specific embodiments when read in connection with the accompanying drawing.

BRIEF DESCRIPTION OF THE DRAWING

FIG. 4 is an end view of the mounting arrangement of FIG. 3;

FIG. 5 is a view in the direction of the arrows A—A of FIG. 4; and

FIG. 6 is an exploded view illustrating the mounting of the primary slit of the arrangement of FIGS. 1 and 2.

DESCRIPTION OF THE PREFERRED EMBODIMENTS

Figure 1:
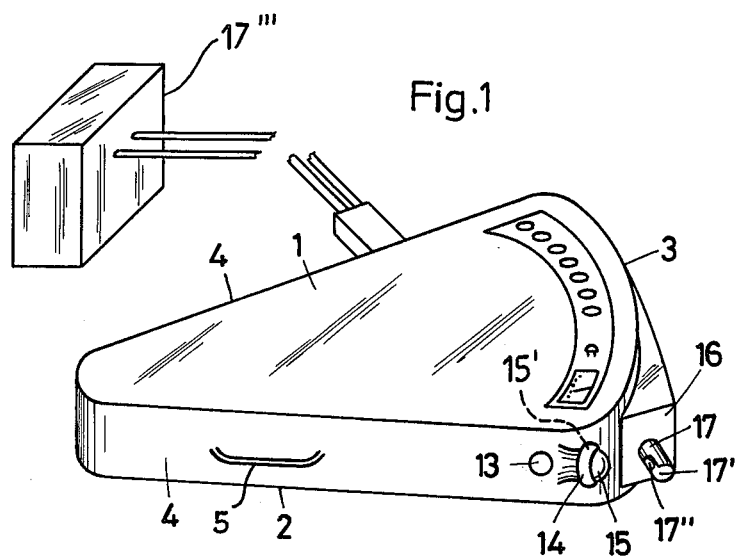
FIG. 1 is a prespective view of an arrangement according to the invention.

Referring first to FIG. 1 of the drawing, it may be seen that this represents a perspective view of an arrangement or device according to the invention for the spectral analysis of substances. The spectrometric device comprises a housing which includes an upper or cover portion 1 and a lower portion 2. The upper portion 1 and the lower portion 2 of the housing are both in the form of a segment of a circle. The housing further includes a back portion 3 which is configurated as a cylindrical section as well as a pair of lateral portions 4 each of which is of plate-like configuration. Only one of the lateral portions 4 of the housing is visible and this is provided with a handle 5 for carrying the device.

Figure 2:
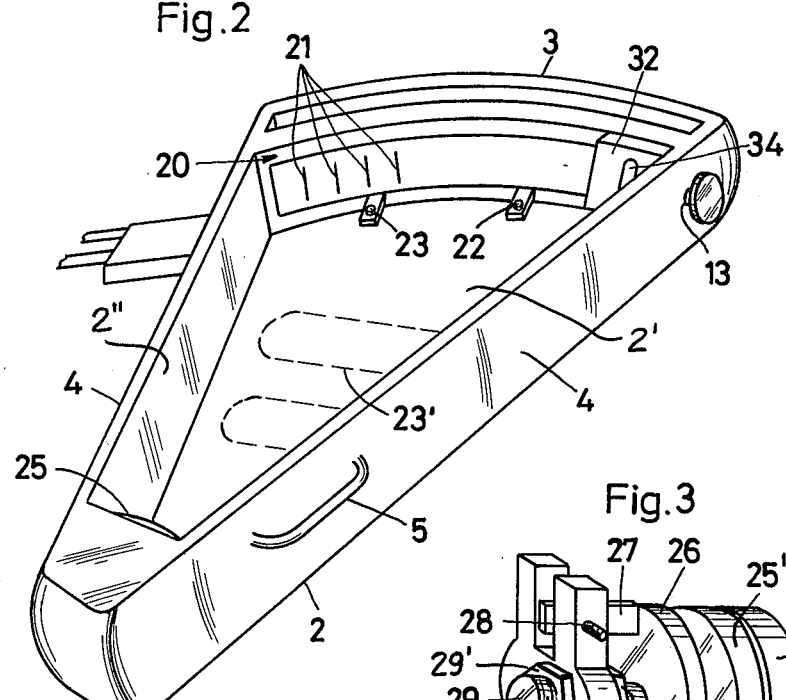
FIG. 2 shows the interior of the arrangement of FIG. 1.

Referring now to FIG. 2 as well as FIG. 1, it will be seen that a concave diffraction grating 25 is mounted inside the housing of the device. In addition, a carrier 32 is mounted inside the housing of the device. The carrier 32 carries a slit 34 and the latter constitutes the primary slit of the device, that is, the radiation derived from a sample being investigated is directed to the grating 25 via the slit 34. A series of secondary slits 21 is provided in a carrying member 20 which is likewise arranged inside the housing of the device.

An adjusting screw 13 for the carrier 32 and the primary slit 34 is provided in the visible lateral portion 4 of the housing of the device and the adjusting screw 13 extends through this lateral portion 4 of the housing. Furthermore, as best seen from FIG. 1, the arcuate back portion 3 of the housing is provided with a mounting 14 having a window 15 through which the radiation derived from a sample being investigated enters the interior of the housing. A lens 15' is arranged inside the mounting 14 behind the window 15 and serves to form an image of the radiation derived from a sample being investigated on the concave grating 25 located inside the housing.

The radiation from a sample being investigated is here derived by means of a spark discharge. For the generation of the spark discharge, a protective housing 16 is mounted on the arcuate back portion 3 of the housing of the device. A protective casing 17 is, in turn, mounted on the protective housing 16. The protective casing 17 concentrically surrounds an electrode 17' which serves to generate the spark discharge. It may be seen that the protective casing 17 is provided with a circular cutout 17" which is directed towards the mounting 14 and the lens 15'. This arrangement of the protective casing 17 and the electrode 17', which is a substitute for the conventional Petrey table, is the subject of the earlier-mentioned copending applications by the same assignee, namely, the application Ser. No. 665,771.

By placing the spectrometric device with the casing 17 on a sample to be investigated, the casing 17 with the cutout 17" forms an exit window for the spark discharge. An image of the spark discharge is then formed on the concave grating 25 via the lens 15' by means of the exit window thus formed. The spark discharge is generated and controlled via a spark overvoltage generating device located in an apparatus 17''' which is connected with the specrometer according to the invention by means of the high-voltage cables illustrated in FIG. 1 but not identified by a reference numeral. The protective casing 17 is a component of a protective circuit which isolates the spark overvoltages generating device located in the apparatus 17''' in the event that the electrode 17', that is, the protective casing 17, does not contact the sample and, at the same time, does not lie at the ground potential of the operating personnel.

A power supply, an analyzer and an overall control system which may be used with an arrangement in accordance with the invention are all subjects of different ones of the earlier-mentioned copending applications by the same assignee, namely, the applications Ser. Nos. 665,771-665,774 filed Mar. 10, 1976.

As is apparent from FIG. 2 in particular, the construction of the spectrometer itself also departs from the constructions used in accordance with the current state of the art. Thus, conventionally, the primary slit and the secondary slits are, together with the grating, mounted on a very massive and heavy frame. In the illustrated construction according to the invention, however, this heavy frame is replaced with a body or base 2' of light metal which is formed into a distortion-resistant supporting unit by means of lateral profiled strips 2".

The supporting unit 2', 2" is elastically suspended at the three points inside the actual housing of the device. The carrying member 20 which is provided with the secondary slits 21 is mounted on the supporting unit 2',2". It may be seen that the carrying member 20 is arcuate and, more particularly, is curved so as to correspond to the curvature of the Rowland circle. Thus, the secondary slits 21, whose positions are or may be aligned in correspondence with the spectral lines of samples to be investigated, lie on a path which follows the arc of the Rowland circle. The carrying member 20 carrying the secondary slits 21 is adjustably mounted on the supporting unit 2', 2" and adjusting screws 22 and 23 are provided for the adjustment of the carrying member 20 on the supporting unit 2',2".

A heating foil 23' is provided at the bottom of the housing of the spectrometric device and enables the housing to be maintained at a higher temperature than the surroundings during operation. In this manner, variations in the temperature of the surroundings may be prevented from changing the existing temperature of the device itself and, concomitantly, thermal expansions and contractions may be avoided.

Figure 3:
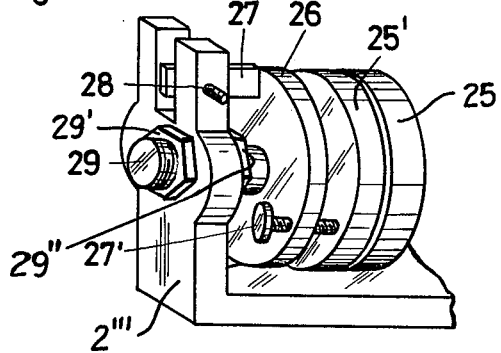
FIG. 3 illustrates the manner in which the concave diffraction grating of the arrangement of FIGS. 1 and 2 is mounted.

The concave grating 25 is, as best seen from FIGS. 3-5 which show the mounting of the concave grating 25 in an enlarged view, mounted on an extension 2'''' of the supporting unit 2', 2". The extension 2'''' extends perpendicularly to the base 2' of the supporting unit 2', 2".

The concave grating 25 is fastened to a cup-shaped member 25'. A bolt 29 extends through the extension 2'''' of the supporting unit 2', 2" and into the cup-shaped member 25', and the bolt 29 is axially displaceable in the extension 2'''' for focusing purposes. A pair of nuts 29' and 29" is provided for axially displacing the bolt 29 in the extension 2''''. A pressure plate 26 is mounted on the bolt 29 and adjusting screws 27', of which only one is shown in FIG. 3, are provided in order to permit tilting of the concave grating 25 with respect to the pressure plate 26. In this manner, the orientation of the axis of the grating 25, which axis normally extends perpendicular to the axis of the Rowland circle, may be adjusted.

The pressure plate 26 carries a tongue 27 which projects into a slot provided in the extension 2'''' of the supporting unit 2', 2". A screw 28 permits the tongue 27 to be locked in position or loosened. By suitable adjustment of the screw 28, the grating 25 may be rotated about its axis. This enables the lines or rulings of the grating 25 to be aligned so that they extend normal to the plane of the spectrometer.

FIG. 6 shows that the primary slit 34 is formed in a member 33 which, in turn, is carried by the carrier 32. It will be seen that the member 33 is here shown as being of plate-like configuration.

FIG. 6 further illustrates a portion of the carrying member 20 in an enlarged perspective view and, in particular, that portion of the carrying member 20 in which the plate 33 with the primary slit 34 is arranged. The plate 33 with the primary slit 34 is arranged in this portion of the carrying member 20 so as to be adjustable or capable of undergoing alignment and so as to be arrestable in any one of a plurality of positions. To this end, the carrying member 20 is provided with an upper web or arm 20' and a lower web or arm 20". Both the upper web 20' and the lower web 20" are formed so as to have a U-shaped profile and, as a result, a groove 30 is formed in the upper web 20' whereas a groove 31 is formed in the lower 20". As indicated by the broken lines, the carrier 32 for the plate 33 with the primary slit 34 is guided in the grooves 30 and 31.

As seen from FIG. 6, the upper end face or edge of the carrier 32 is provided with a pair of blind holes 35 whereas the lower end face or edge of the carrier 32 is provided with a pair of spherical recesses 36. A spherical member 37 is accommodated in each of the holes 35 and in each of the recesses 36 and the spherical members 37 are freely rotatable in the respective holes 35 and the respective recesses 36. In addition to the spherical members 37, a biasing element or spring 39 is accommodated in each of the holes 35 so that the spherical members 37 which are located in the holes 35 are directly subjected to a biasing action.

In order to permit adjustment or alignment of the carrier 32 to be effected, the carrying member 20 is provided with an abutment 41. The abutment 41 is, in turn, provided with a spring member 32' on that side thereof which is directed towards the carrier 32. Another abutment 45 is provided on that side of the carrier 32 opposite the side thereof which faces the abutment 41. As indicated by the screws in FIG. 6 which have not been identified by reference numerals, the abutment 45 may be mounted on the carrying member 20 by means of screws. The abutment 45 guides the adjusting screw 13 visible in FIGS. 1 and 2 and it will be seen that the adjusting screw 13 is arranged to act upon that side of the carrier 32 opposite the side thereof which faces the abutment 41. As is evident from FIGS. 1 and 2, the adjusting screw 13 extends through one of the side walls or lateral portions 4 of the housing of the spectrometric device so as to be accessible from exteriorly of the housing. It will be appreciated from the construction just outlined that the carrier 32 may be adjusted between the two abutments 41 and 45.

As shown in FIG. 6, the carrying member 20 is provided with a transparent window 47 in the region thereof where the carrier 32 for the primary slit 34 is arranged.

By virtue of the adjusting means for the primary slit 34 and the grating 25 which is provided by the invention, as well as by virtue of the utilization of a light supporting units 2', 2" according to the invention, it becomes possible to construct the spectrometer as a handy portable device, especially when operation is not carried out under vacuum. The device for generating the spark discharge may likewise be made portable by suitable dimensioning. Furthermore, due to the incorporation of protective or breaker circuits which prevent the generation of a spark discharge if the sample to be investigated and the casing 17 which is constructed as a safety contact are not simultaneously at ground potential, care is taken that the operating personnel are protected against the high voltages generated by the electronic auxiliary devices. The construction of a spark gap with protective circuits is the subject of another application by the same assignee, namely, the earlier-mentioned application Ser. No. 665,772 filed Mar. 10, 1976, and is accordingly not described here in further detail.

It will be understood that each of the elements described above, or two or more together, may also find a useful application in other types of constructions and operations differing from the types described above.

While the invention has been illustrated and described as embodied in an arrangement for the spectral analysis of metals by generating a spark discharge, it is not intened to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for spectroscopically analyzing the composition of a workpiece, comprising, a portable support;

means including an electrode juxtaposable with a surface of said workpiece for sparking between said surface and said electrode;

optical means on said support for transmitting into said support the light of a spark between said electrode and said surface;

a reflective Rowland grating in said support defining therein a Rowland circle;

an arcuate guide in said support having a pair of spaced parallel walls conforming to and extending along said Rowland circle;

a carrier displaceable along said guide between said walls and dimensioned to have some freedom of movement in direction towards and away from said walls;

means including a primary slit on said carrier displaceable therewith along said Rowland circle for casting the light from said optical means on said Rowland grating;

means including at least one guide spring located intermediate and bearing upon said carrier and one of said walls of said guide for urging said carrier against the other of said walls;

a fixed abutment on said support adjacent said circle;

an abutment spring mounted on said fixed abutment and extending generally in one direction along said circle from said fixed abutment;

a movable abutment displaceable along said circle in said one direction and in another direction opposite said one direction, said carrier being between said abutments and being engageable in said one direction with said movable abutment and in said other direction with said abutment spring;

means for displacing said movable abutment in said directions along said circle and for arresting said movable abutment at any of a multiplicity of positions therealong, whereby said carrier is limitedly movable along said guide between said movable abutment and said spring when embraced thereby; and means including a plurality of secondary slits spaced apart and fixed on said support at said Rowland circle for breaking the light reflected by said Rowland grating down into an analyzable spectrum.

2. The apparatus defined in claim 1, wherein said walls are formed with respective grooves facing toward each other.

3. The apparatus defined in claim 2, wherein said carrier is provided with at least one rolling element engaging each of said grooves.

4. The apparatus defined in claim 3, wherein said guide spring is a compression spring braced between one of said rolling elements and said carrier.

5. The apparatus defined in claim 4, wherein said carrier has two such rolling elements engaging each of said grooves.

6. The apparatus defined in claim 5, wherein said carrier is formed with two pairs of open recesses each receiving a respective rolling element, said elements being balls.

7. The apparatus defined in claim 1, wherein said means for displacing includes a screw engaging said movable abutment and said support.

* * * * *